US012059167B2

(12) United States Patent
Vogtherr

(10) Patent No.: US 12,059,167 B2
(45) Date of Patent: Aug. 13, 2024

(54) METHOD FOR SIMPLE PRODUCTION OF AN INSTRUMENT SPRING OPTIMIZED IN TERMS OF CLEANING

(71) Applicant: Aesculap AG, Tuttlingen (DE)

(72) Inventor: Robert Vogtherr, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 522 days.

(21) Appl. No.: 17/439,852

(22) PCT Filed: Mar. 3, 2020

(86) PCT No.: PCT/EP2020/055486
§ 371 (c)(1),
(2) Date: Sep. 16, 2021

(87) PCT Pub. No.: WO2020/187553
PCT Pub. Date: Sep. 24, 2020

(65) Prior Publication Data
US 2022/0183710 A1 Jun. 16, 2022

(30) Foreign Application Priority Data
Mar. 18, 2019 (DE) ...................... 10 2019 106 852.5

(51) Int. Cl.
*A61B 17/28* (2006.01)
*A61B 17/3201* (2006.01)
(52) U.S. Cl.
CPC ...... *A61B 17/2841* (2013.01); *A61B 17/3201* (2013.01); *A61B 2017/2845* (2013.01)
(58) Field of Classification Search
CPC ................ B25B 7/02; B25B 7/04; B25B 7/18
(Continued)

(56) References Cited

U.S. PATENT DOCUMENTS 439,994 A * 11/1890 Ballard .................. A61B 17/10
  294/93
736,964 A * 8/1903 Hanson .................... G04D 1/08
  29/232
(Continued)

FOREIGN PATENT DOCUMENTS

DE       10137915 B4    7/2004
DE  102007030874 B4    4/2009
(Continued)

OTHER PUBLICATIONS

Office Action received in Japanese Application No. 2021-556329 dated Mar. 2, 2023, with translation, 3 pages.
(Continued)

*Primary Examiner* — Jason L Vaughan
(74) *Attorney, Agent, or Firm* — Christopher A. Rothe; Culhane PLLC

(57) ABSTRACT

A method for producing a medical hand-held instrument having two grip elements, pivotable relative to each other, and a spring element, with the method steps to be performed in the following sequence: providing the two grip elements each with a pivot-pin receiver eyelet formed thereon, at their one end portion and an articulation eyelet for the spring element formed thereon, providing the spring element with pivot pins arranged at or formed integrally with each spring end, inserting the pivot pins of the spring element into the articulation eyelets of the grip elements not yet pivotally coupled to each other, and bringing together the grip elements in the region of their pivot pin receiver eyelets and pivotally coupling the grip elements by inserting a pivot pin into the overlapping pivot pin receiver eyelets.

12 Claims, 2 Drawing Sheets

(58) Field of Classification Search
USPC .................................. 81/302, 427, 417, 354
See application file for complete search history.

(56) References Cited

U.S. PATENT DOCUMENTS

| | | | | |
|---|---|---|---|---|
| 1,636,448 | A * | 7/1927 | Whipple | B25B 7/02 29/268 |
| 4,124,929 | A * | 11/1978 | Roux | B25B 7/04 968/665 |
| 4,462,403 | A * | 7/1984 | Martin | A61B 17/8866 30/190 |
| 4,733,663 | A * | 3/1988 | Farley | A61B 17/32 606/171 |
| 4,898,157 | A * | 2/1990 | Messroghli | A61B 17/062 606/147 |
| 4,990,148 | A * | 2/1991 | Worrick, III | A61B 17/1611 606/83 |
| 5,314,431 | A * | 5/1994 | Graziano | A61B 17/8863 606/103 |
| 5,766,177 | A * | 6/1998 | Lucas-Dean | A61B 17/1611 606/184 |
| 6,517,545 | B1 * | 2/2003 | Mazur | A61B 17/1606 606/174 |
| 6,702,820 | B2 * | 3/2004 | Mazur | A61B 17/1606 606/174 |
| 7,611,517 | B2 * | 11/2009 | Lim | A61B 17/7086 606/86 A |
| 7,625,376 | B2 * | 12/2009 | Brumfield | B25B 7/14 606/86 A |
| 2003/0083747 | A1 | 5/2003 | Winterbottom et al. | |
| 2005/0222588 | A1 | 10/2005 | Vandenbroek et al. | |
| 2010/0222800 | A1 | 9/2010 | Rebstock et al. | |
| 2013/0211442 | A1 * | 8/2013 | Karim | A61B 17/3201 606/200 |
| 2016/0331396 | A1 * | 11/2016 | Schweitzer | A61B 17/320016 |
| 2017/0367721 | A1 | 12/2017 | Storz et al. | |
| 2018/0161028 | A1 * | 6/2018 | Bosshard | A61B 17/32053 |
| 2020/0138462 | A1 | 5/2020 | Vogtherr | |

FOREIGN PATENT DOCUMENTS

| | | |
|---|---|---|
| DE | 202009001809 U1 | 4/2009 |
| DE | 202009002433 U1 | 4/2009 |
| DE | 202010007995 U1 | 9/2010 |
| DE | 202011052256 U1 | 1/2012 |
| DE | 102014102606 A1 | 8/2015 |
| DE | 102017114260 A1 | 12/2018 |
| JP | S53128086 A | 11/1978 |

OTHER PUBLICATIONS

Written Opinion received in International Application No. PCT/EP2020/055486 dated May 18, 2020, with translation, 12 pages.
Search Report received in German Application No. 10 2019 106 852.5 dated Feb. 10, 2020, with translation, 11 pages.
Search Report received in International Application No. PCT/EP2020/055486 dated May 18, 2020, with translation, 7 pages.
Office Action received in Chinese Application No. 202080020391.7 dated Feb. 29, 2024, with translation, 12 pages.

\* cited by examiner

METHOD FOR SIMPLE PRODUCTION OF AN INSTRUMENT SPRING OPTIMIZED IN TERMS OF CLEANING

CROSS-REFERENCE TO RELATED APPLICATIONS

This application is the United States national phase entry of International Application No. PCT/EP2020/055486, filed Mar. 3, 2020, and claims the benefit of priority of German Application No. 10 2019 106 852.5, filed Mar. 18, 2019. The contents of International Application No. PCT/EP2020/055486 and German Application No. 10 2019 106 852.5 are incorporated by reference herein in their entireties.

FIELD

The present invention relates to a method for producing a medical hand-held instrument, in particular a method for producing a surgical hand-held instrument of the forceps or scissors type, having two grip elements or handle bars which can be pivoted relative to each other, and a spring element, preferably a leaf spring which is bent in a U shape or V shape, which has two spring element ends which are each connected to one of the two grip elements, so that when at least one of the two grip elements is pivoted out of a basic position, pivoting back into the basic position can be effected via the spring element.

BACKGROUND

DE 10 2017 114 260 A1 shows a medical hand-held instrument with two grip elements, which are pivotable relative to each other, and a spring element, which has two spring element ends. The spring element ends are each connected to one of the two grip elements, so that when at least one of the two grip elements is pivoted out of a basic position, it can be pivoted back into the basic position via the spring element. The hand-held instrument is characterized by the fact that at least one of the two spring element ends is connected to the corresponding grip element via a form fit, which is created by forming the spring element. Furthermore, DE 10 2017 114 260 A1 discloses a method for producing a medical hand-held instrument.

In document DE 20 2010 007 995 U1 an instrument is disclosed in which a one-piece leaf spring is screwed to one side of the instrument or instrument handle and rests with its free end on the opposite side of the instrument or on the other instrument handle. This has several disadvantages: in general, threads should be avoided as much as possible in surgical instruments, since the gaps between the nut thread and the screw are virtually impossible to clean. In the instrument according to document DE 20 2010 007 995 U1, the leaf spring abuts directly against the inside of the instrument in the area of the screw connection, which also results in a very narrow, non-cleanable gap between the leaf spring and the instrument. Moisture or cleaning fluid can dry very poorly in this gap and can have a corrosive effect over a period of time. In addition, the leaf spring is pierced in this corrosion-prone area and its geometry is weakened, which means that the leaf spring is at risk of breaking at this point. The free end of the leaf spring rubs in the support area on the opposite side of the instrument during movement or use of the instrument. In the long term, this friction deteriorates the surface quality of the support area and also increases the susceptibility to corrosion there.

Document DE 20 2009 002 433 U1 discloses an instrument with two grip branches, in which one screwed-on leaf spring part is provided for each grip branch. The two leaf spring parts are supported against each other to cause the two handle branches to swing back into a basic position. With regard to its cleanability, the instrument according to document DE 20 2009 002 433 U1 has the same disadvantages as the instrument according to document DE 20 2010 007 995 U1, in particular because of its screw connections. Furthermore, there is a plug-in connection in the contact area of the two free leaf spring ends, which is relatively sharp-edged. Since this point is located in the middle of the easily accessible handle area of the instrument, a user's surgical glove can easily be cut or damaged here. And even if this connection point is well deburred when the instrument is new, a certain amount of abrasion and burr will form after several uses.

The two preceding documents DE 20 2010 007 995 U1 and DE 20 2009 002 433 U1 are also complex and delicate to produce. The screw for fastening the spring is screwed through the hole in the leaf spring into the thread in the handle. During this step, it is important to tighten the screw with sufficient torque to prevent it from loosening due to transport, vibrations or instrument movements. This cannot be guaranteed, especially if the thread is dirty and thus hinders movement. Furthermore, the spring mechanism is easy to replace, but equally easy to manipulate. A user can simply loosen the screw for cleaning. However, following the cleaning, it is not ensured that he also properly reattaches the screw. In addition, the screw may be lost and may cause disruptions in the clinical workflow.

Document DE 20 2009 001 809 U1 refers to an instrument whose spring mechanism, as in the instrument according to document DE 20 2009 002 433 U1, consists of two screwed leaf spring parts. In order to avoid at least the mentioned disadvantages of a sharp-edged plug-in connection point, a ball and socket geometry is provided between the leaf spring parts. However, due to the screw connections and the ball and socket geometry, the instrument according to DE 20 2009 001 809 U1 is still disadvantageous in terms of its cleanability. In addition, the spring mechanism according to DE 20 2009 001 809 U1 is complex to produce because the geometries shown have to be welded to the free leaf spring ends or have to be complexly milled.

Document DE 20 2011 052 256 U1 describes an instrument whose spring mechanism consists of a screwed leaf spring part and an attached second part articulated to its free end. Due to the screw connection and the complexity of the spring mechanism, the instrument according to document DE 20 2011 052 256 U1 is also relatively difficult to clean and requires effort to produce.

Instruments in which the spring mechanisms are at least partially integral with corresponding handle parts in a complex manner are described, for example, in documents DE 101 37 915 B4, DE 10 2007 030 874 B4 or DE 10 2014 102 606 A1. Further examples of such instruments are disclosed in documents US 2005/222 588 A1 or US 2003/083 747 A1. These instruments are disadvantageous not only because of their complex production but also because of the poor replaceability or dismantlability of the leaf spring parts.

SUMMARY

In view of the production methods of instruments according to the aforementioned prior art, it is an object of the present invention to provide a cost-saving and time-saving method for producing a hand-held medical instrument that is easy to clean, has relatively low wear, and/or is relatively easy to repair.

The present invention thus relates to a method for producing a hand-held medical instrument having two grip elements/grip branches (grip handles, grip levers, lever arms) which can be pivoted relative to each other and a spring element (pretensioning spring) which is preferably bent in a U shape or V shape, in particular of leaf spring design. Each of the two ends of the spring element (spring element ends) is then connected to a corresponding one of the two grip elements. The two grip elements are then connected to each other in such a way that when at least one of the two grip elements is pivoted out of a basic position relative to the other grip element, it can be pivoted back into the basic position via the spring element.

In other words, the present method for producing a hand-held medical instrument provides, inter alia, the following method steps in the order indicated:

(a) providing two preferably identically constructed (instrument) grip elements, each having a pivot-pin receiver eyelet formed thereon, at their one end portion and an articulation eyelet for a spring element, preferably of the leaf spring design, formed thereon, further preferably slotted in its central portion, b) providing the spring element with pivot pins arranged at each spring end or preferably formed integrally with the spring element, c) inserting the pivot pins of the spring element into the articulation eyelets of the instrument grip elements not yet pivotally coupled to each other, and d) bringing together the instrument grip elements in the region of their pivot-pin receiver eyelets and pivotally coupling the instrument grip elements by inserting a preferably rivet-shaped or screw-shaped pivot pin into the overlapping/aligned pivot pin receiver eyelets.

This procedure simplifies the assembly of the medical hand-held instrument and makes the instrument properties, in particular the spring preload, reproducible.

The method for producing the medical instrument according to the invention is characterized in particular by the fact that the insertion of the pivot pin of the spring element into the articulation eyelets is carried out prior to the merging and pivot coupling of the grip elements. In other words, the spring element is or will be formed such that it can hook onto the corresponding grip element without having to be formed before, during or after hooking.

In a preferred embodiment, the form-fit connection of the two spring element ends with the corresponding grip elements can thus be secured by connecting the two grip elements. This ensures safe handling of the medical hand-held instrument without requiring an additional work step.

Preferably, moreover, the two grip elements may be connected and disconnected in a form-fitting manner so that the medical hand-held instrument can be disassembled for cleaning or repair simply by disconnecting the grip element connection.

According to the invention, the articulation eyelet/receptacle may be designed in the production method in such a way that it receives the corresponding spring element end in a form-fitting manner according to a lock-and-key principle. The receptacles may be essentially ring-shaped and each may have a slit portion through which the corresponding spring element end can be inserted into the associated receptacle. Furthermore, two opposite recesses may be formed on each of the spring element ends, which grip around the spring element ends after they have been inserted into the receptacle.

In other words, the spring element ends may each have two opposite recesses, so that the spring element ends each have a T-shaped end portion as a pivot pin. The crossbar of the T-shaped end portion may serve as a pivot axis in each case.

BRIEF DESCRIPTION OF THE DRAWING FIGURES

The present invention is described in more detail below by way of a preferred configuration example with reference to the accompanying drawings. They show:

Identical or functionally equivalent features are marked with the same reference signs in the individual figures.

DETAILED DESCRIPTION

Figure 1:
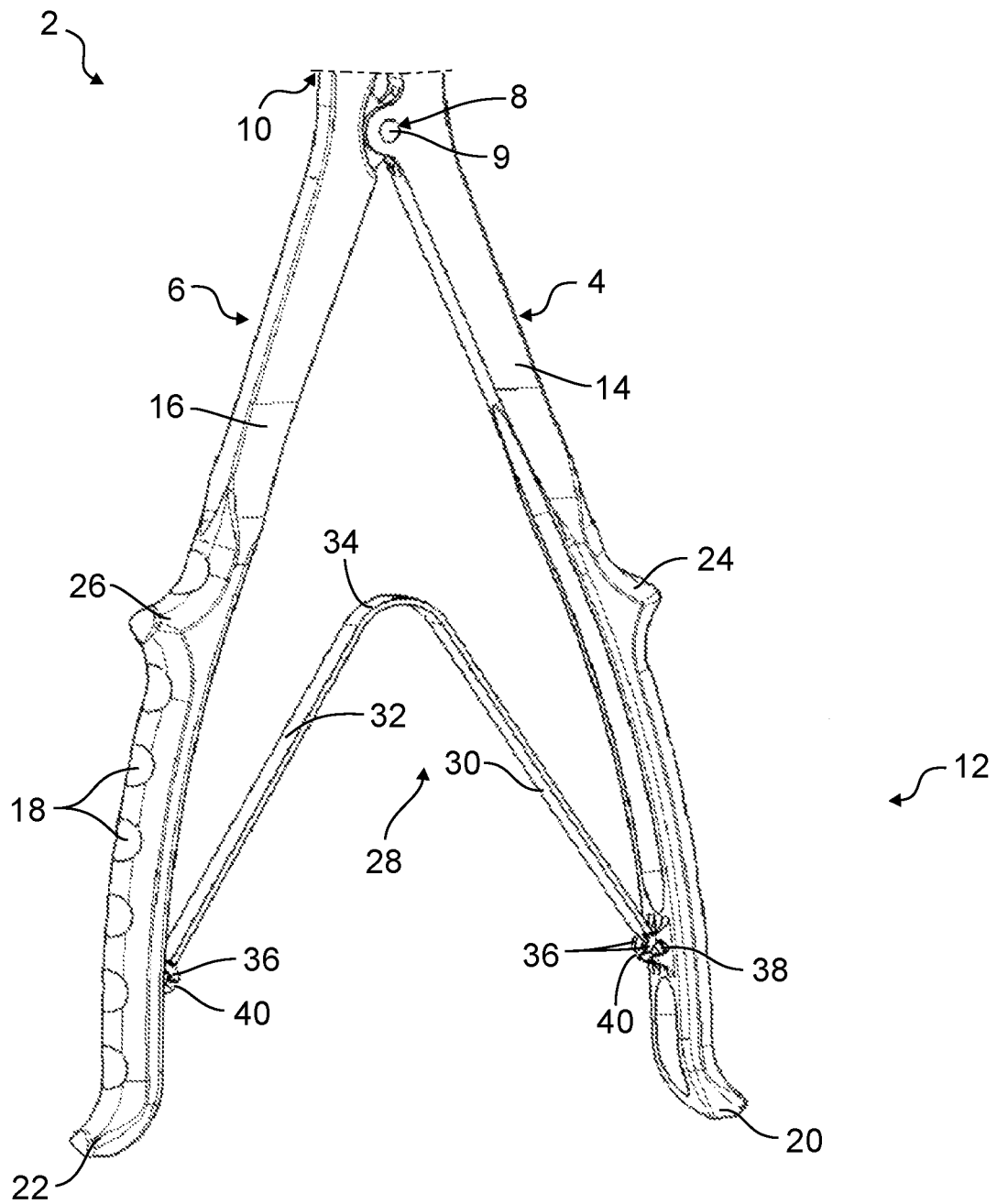
FIG. 1 shows a detailed perspective view of a hand-held medical instrument produced by a method according to the invention, in accordance with a preferred embodiment.

FIG. 1 shows a medical hand-held instrument 2 according to a preferred embodiment. The hand-held instrument 2 is of the forceps or scissors type. This means that it has two lever/instrument branches 4 and 6 which are pivotably connected to each other via a hinge 8. For this purpose, the levers 4 and 6 each have a (pivot-pin) receiver eyelet in the area of the hinge 8, which are brought together for mounting the medical hand-held instrument 2 in such a way that their central axes are substantially aligned. As described below, after bringing together the levers 4 and 6, a rivet 9 is passed through the receiver eyelets and thus the two levers 4 and 6 are connected to each other via the hinge 8. The rivet 9 here is an example of a 'pivot pin':

The portion of the hand-held instrument 2 on one side (distal side) of the hinge 8 is a jaw portion 10 (shown only in part). The portion on the other side (proximal side) of the hinge 8 is a handle portion 12. The proximal parts of the levers 4 and 6, which form the handle portion 12 of the hand-held instrument 2, are hereinafter referred to as grip elements 14 and 16.

The grip element 14 of the lever 4 and the grip element 16 of the lever 6 are essentially symmetrical to each other. Both grip elements 14 and 16 have an indentation 18 adapted to a human hand on the side facing away from the other grip element 16 and 14, respectively, in order to ensure good haptics when gripping the hand-held instrument 2. On the proximal side of the handle portion 12, at the free ends of the grip elements 14 and 16, the grip elements 14 and 16 have grip projections 20 and 22 on the side facing away from the respective other grip element 16 and 14. Likewise, a hand's width away from each of the free ends, the grip elements 14 and 16 have grip projections 24 and 26 on the side facing away from the other grip element 16 and 14. The grip projections 20 and 24 or 22 and 26 each delimit an area on the grip elements 14 and 16 at which a user preferably grips or should preferably grip the handle portion 12. The grip projections 20 and 24 or 22 and 26 are intended to prevent the user's fingers from slipping.

A spring element 28 is provided between the grip elements 14 and 16. The spring element 28 is essentially U shaped or V shaped and has two legs 30 and 32, which are connected to each other via an arcuate portion 34.

The two legs 30 and 32 and the arcuate portion 34 are formed in one piece in the form of a curved leaf spring, preferably made of spring steel.

Figure 2:
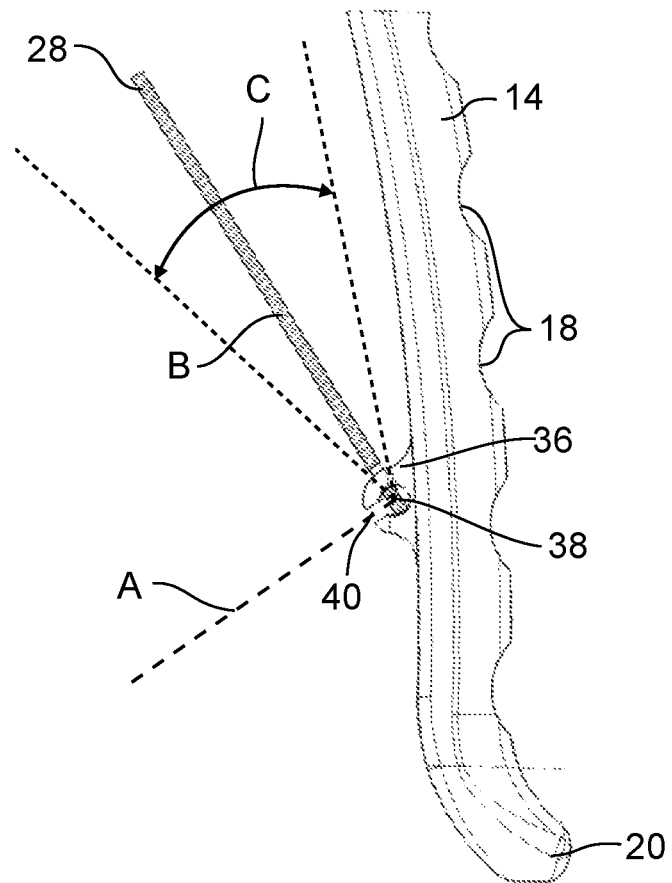
FIG. 2 shows a detailed perspective view of the hooking of the spring element end with the grip element according to the preferred embodiment.
Figure 3:
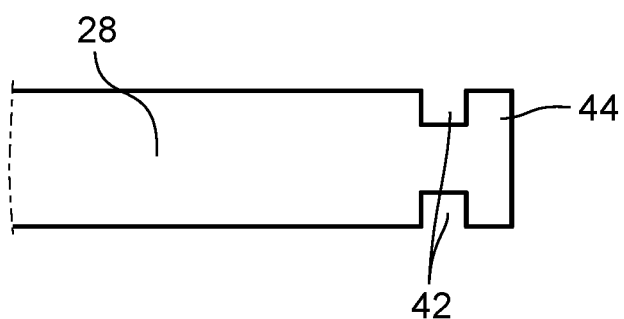
FIG. 3 shows a top view of the spring element end according to the preferred embodiment.

FIGS. 2 and 3 show in detail the hooking of one of the two spring element ends with the corresponding grip element 14, 16 and the design of the spring element end in the medical hand-held instrument 2 produced according to the invention. It should be noted that FIG. 2 is not a sectional view, but the hatching of the spring element 28 is rather for better clarity. Furthermore, only the connection between the leg 30 of the spring element 28 and the grip element 14 is shown in FIG. 2. However, it goes without saying that the connection between the leg 32 and the grip element 16 is the same.

On the side facing the other grip element 16 (not shown), the grip element 14 has two projections/receptacles/articulation eyelets 36 extending in the direction of the other grip element 16, said eyelets 36 extending parallel to the direction in which the grip element 14 extends. At their respective free ends, the receptacles 36 each have a bearing eye 38 with a respective slit 40 extending to the edge of the respective receptacle 36. The width of the slit 40 is only slightly larger than the thickness of the spring element 28.

A connecting portion of the spring leaf-shaped spring element 28 has, as shown in FIG. 3, two recesses/punchings 42 arranged to form a T-shaped end portion 44 on the spring element 28. In other words, the connecting portion has two projections arranged to form the T-shaped end portion 44. The crossbar of the T-shaped end portion 44 serves as a pivot axis for the spring element 28 when assembled. The T-shaped end portion 44 is thus an example of a 'pivot pin' of the spring element 28.

For hooking the spring element 28 to the corresponding grip element 14 according to the preferred embodiment, the crossbar of the T-shaped end portion 44 is inserted through the slit 40 into the bearing eye 38. During this insertion, the leg 30 of the spring element 28 inevitably has to be oriented parallel to the slit 40 (see indicated assembly position A in FIG. 2). The same has to be done with the other grip element 16 (not shown) in order to mount the spring element 28.

Finally, in order to firmly hook or latch the spring element 28 to the grip elements 14, 16, the two grip elements 14, 16 are connected to each other at the hinge 8. In the production method according to the preferred embodiment, the two grip elements 14, 16 are riveted to each other at the hinge 8. However, this connection can also be implemented in any other way, e.g. as a screw connection.

In other words, according to the invention, the spring element 28 is first hooked with a spring element end of the respective leg 30, 32 in the receptacle of the corresponding grip element 14, 16 and subsequently this hooking is fixed and secured by connecting the two grip elements 14, 16 on the hinge 8 with the rivet 9.

The fact that the crossbar is trapped in the bearing eyes 38 and can no longer be moved through the slit 40 (see basic position B in FIG. 2) is maintained until the legs 30, 32 of the spring element 28 are not deliberately pivoted into the assembly position A. However, such pivoting of the legs 30, 32 of the spring element 28 into the assembly position A can only occur in the event of deliberate bending of the spring element 28 or loosening of the connection between the grip elements 14, 16.

In particular, in a normal pivoting range C (see FIG. 2), in which the legs 30, 32 of the spring element 28 move when the hand-held instrument 2 is used, the end portions of the spring element 28 remain trapped in the receptacles 36 or bearing eyes 38 of the grip elements 14, 16.

The embodiment of the hand-held medical instrument produced by the method according to the invention shown in FIGS. 1 to 3 and described above is only one example of a possible implementation.

The invention claimed is:

1. A method for producing a hand-held medical instrument which has two grip elements that are couplable to one another in a pivotable relationship and a spring element, the method comprising the steps of:
   providing the two grip elements each with a pivot-pin receiver eyelet formed thereon, at their one end portion and an articulation eyelet for the spring element formed thereon;
   providing the spring element with pivot pins arranged at each spring end;
   inserting the pivot pins into the articulation eyelets;
   bringing the grip elements together at their pivot pin receiver eyelets, after inserting the pivot pins into the articulation eyelets, so that the pivot pin receiver eyelets overlap; and
   pivotally coupling the grip elements to one another by inserting a hinge pin into the pivot pin receiver eyelets after the pivot pin receiver eyelets overlap.

2. The method according to claim 1, wherein the spring element comprises a spring formed by a first leg and a second leg connected to the first leg.

3. The method according to claim 2, wherein each pivot pin-receiver eyelet comprises a projection that defines a bearing eye opening and a slit extending from the bearing eye opening to a peripheral edge of the projection.

4. The method according to claim 3, wherein the step of inserting the pivot pins into the articulation eyelets comprises orienting the first and second legs in an assembly position, in which the pivot pins are passable through the slits into the bearing eye openings.

5. The method according to claim 4, further comprising, after inserting the pivot pins into the articulation eyelets, the step of orienting the first and second legs in a basic position, in which the pivot pins are not passable through the slits and remain trapped in the bearing eye openings.

6. The method according to claim 5, wherein the first and second legs of the spring are detained in the basic position after the step of pivotally coupling the grip elements to one another to inhibit orienting of the pivot pins back to the assembly position.

7. A method for producing a hand-held medical instrument having a first grip element, a second grip element, and a spring element, the method comprising the steps of:
   providing a first pivot-pin receiver eyelet and a first articulation eyelet on the first grip element;
   providing a second pivot-pin receiver eyelet and a second articulation eyelet on the second grip element;
   providing a first pivot pin at a first end of the spring element;
   providing a second pivot pin at a second end of the spring element;
   inserting the first pivot pin into the first articulation eyelet;
   inserting the second pivot pin into the second articulation eyelet;
   overlapping the first pivot-pin receiver eyelet with the second pivot-pin receiver eyelet after the first pivot pin is inserted into the first articulation eyelet and the second pivot pin is inserted into the second articulation eyelet; and inserting a pivot pin through the first pivot-pin receiver eyelet and the second pivot-pin receiver eyelet to pivotally couple the grip elements together.

8. The method according to claim 7, wherein the spring element comprises a spring formed by a first leg and a second leg connected to the first leg.

9. The method according to claim 8, wherein the first and second pivot pin-receiver eyelets each comprise a projection that defines a bearing eye opening and a slit extending from the bearing eye opening to a peripheral edge of the projection.

10. The method according to claim 9, wherein the steps of inserting the first pivot pin into the first articulation eyelet and inserting the second pivot pin into the second articulation eyelet comprise orienting the first and second legs in an assembly position, in which the first and second pivot pins are passable through the slits into the bearing eye openings.

11. The method according to claim 10, further comprising, after inserting the first pivot pin into the first articulation eyelet and inserting the second pivot pin into the second articulation eyelet, the step of orienting the first and second legs in a basic position, in which the first and second pivot pins are not passable through the slits and remain trapped in the bearing eye openings.

12. The method according to claim 11, wherein the first and second legs of the spring are detained in the basic position after the grip elements are pivotally coupled to one another to inhibit orienting of the pivot pins back to the assembly position.

* * * * *